(12) United States Patent
Baudry et al.

(10) Patent No.: US 11,396,017 B2
(45) Date of Patent: Jul. 26, 2022

(54) METHOD AND SYSTEM FOR RECOVERING PRODUCTS FROM AN EMULSION

(71) Applicant: ECOLE SUPERIEURE DE PHYSIQUE ET DE CHIMIE INDUSTRIELLES DE LA VILLE DE PARIS, Paris (FR)

(72) Inventors: Jean Baudry, Paris (FR); Jérôme Bibette, Paris (FR); Laurent Boitard, Paris (FR); Klaus Eyer, Paris (FR); Krzysztof Langer, Palaiseau (FR)

(73) Assignee: ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 902 days.

(21) Appl. No.: 16/093,914

(22) PCT Filed: Apr. 14, 2017

(86) PCT No.: PCT/EP2017/059070
§ 371 (c)(1),
(2) Date: Oct. 15, 2018

(87) PCT Pub. No.: WO2017/178652
PCT Pub. Date: Oct. 19, 2017

(65) Prior Publication Data
US 2019/0111432 A1    Apr. 18, 2019

(30) Foreign Application Priority Data
Apr. 15, 2016 (FR) .................................. 1653381

(51) Int. Cl.
| B01L 3/00 | (2006.01) |
| G01N 15/14 | (2006.01) |
| C12Q 1/6804 | (2018.01) |
| G01N 33/50 | (2006.01) |
| G01N 15/00 | (2006.01) |

(52) U.S. Cl.
CPC .......... *B01L 3/502784* (2013.01); *B01L 3/54* (2013.01); *C12Q 1/6804* (2013.01); *G01N 15/1456* (2013.01); *G01N 15/1459* (2013.01); *G01N 15/1484* (2013.01); *G01N 33/5094* (2013.01); *B01L 2200/0652* (2013.01); *B01L 2300/021* (2013.01); *B01L 2300/0816* (2013.01); *B01L 2300/123* (2013.01); *B01L 2300/16* (2013.01); *B01L 2300/168* (2013.01); *G01N 2015/003* (2013.01); *G01N 2015/149* (2013.01)

(58) Field of Classification Search
CPC . B01L 3/502784; B01L 3/54; G01N 15/1456; G01N 33/5094; G01N 15/1459; G01N 15/1484; C12Q 1/6804
See application file for complete search history.

(56) References Cited

U.S. PATENT DOCUMENTS

| 8,283,308 B2 | 10/2012 | Mason et al. |
| 8,798,341 B2 | 8/2014 | Baudry et al. |
| 9,513,207 B2 | 12/2016 | Smith et al. |
| 9,981,230 B2 | 5/2018 | Link et al. |
| 2010/0055677 A1 | 3/2010 | Colston, Jr. et al. |

FOREIGN PATENT DOCUMENTS

| CN | 104198709 | 12/2014 |
| EP | 2556883 | 2/2013 |
| JP | 2010133720 | 6/2010 |
| WO | WO 2007/081385 | * 7/2007 |
| WO | WO 2015/157369 | * 10/2015 |

OTHER PUBLICATIONS

International Search Report for PCT/EP2017/059070, dated Jul. 19, 2017.
Written Opinion of the International Search Authority for PCT/EP2017/059070, dated Jul. 19, 2017.
Preliminary Search Report for FR1653381, dated Nov. 30, 2016.

* cited by examiner

*Primary Examiner* — Narayan K Bhat
(74) *Attorney, Agent, or Firm* — B. Aaron Schulman, Esq.; Stites & Harbison, PLLC

(57) ABSTRACT

The present invention relates to a method for selecting and recovering products, comprising the following steps:
  providing an emulsion (6) comprising a plurality of drops (4) contained in a carrier fluid (10), each drop comprising an internal fluid (8),
  measuring at least one physical parameter for several drops (4) of the emulsion (6),
  classifying at least some of the drops (4) of the emulsion in a class based on measurements obtained during the measuring step,
  tagging at least some of the classified drops (4) based on the class of the drop (4),
  selectively recovering the drop (4) or part of the drop (4) using the tag of the drop or part of the drop (4).

13 Claims, 7 Drawing Sheets

METHOD AND SYSTEM FOR RECOVERING PRODUCTS FROM AN EMULSION

The present invention relates to a method for selecting and recovering products. Such a method is for example intended for recovering a particular product contained in certain drops of an emulsion. For example, the product may result from a chemical reaction or a biological reaction having taken place in the drop.

It is known to use flow cytometry systems to characterize isolated particles, in particular cells, driven by a liquid or gaseous flow, before sorting them. However, such systems require a stream of particles to be sorted and simply make it possible to perform simple measurements before recovery. These systems are in particular used to sort cells having membrane or intracellular markers. However, they do not make it possible to sort the cells based on the molecules that they secrete. Furthermore, these systems do not make it possible to perform several measurements successively. Thus, these systems are not well suited to characterizing products by monitoring kinetic reactions. It is therefore not possible to use such systems to select particles or drops based on multiple parameters, like in the case of selecting cells based on complex phenotypes.

Document WO 2010/007307 A2 describes a method for reading an emulsion in a chamber, making it possible to obtain rich information on the content of the drops. After the measurement, a specific drop, having particular characteristics, may be recovered individually by withdrawal using a micro-pipette aspirating the specific drop.

However, the specific drops being disseminated at different points of the emulsion, the recovery is laborious and difficult to automate. Furthermore, aspirating a drop of the emulsion using the micropipette requires removing the upper wall of the chamber containing the emulsion. This step creates risks of evaporation and contamination of the drops that may result in a deterioration of the product to be recovered.

One aim of the invention is to provide a method for selecting and recovering products that is more reliable and faster than the existing methods, allowing a precise characterization and efficient recovery of the content of interest of a drop.

To that end, the invention relates to a method for selecting and recovering products comprising the following steps:

providing an emulsion comprising a plurality of drops contained in a carrier fluid, each drop comprising an internal fluid, measuring at least one physical parameter for several drops of the emulsion, classifying at least some of the drops of the emulsion in a class based on measurements obtained during the measuring step, tagging at least some of the classified drops based on the class of the drop, and selectively recovering the drop or part of the drop using the tag of the drop or part of the drop.

The method according to the invention may comprise one or more of the following features, considered alone or according to any technically possible combination:

a plurality of drops are classified simultaneously during the classification step and the recovery step includes sorting the drops after tagging each classified drop;

the measuring step comprises measuring at least one parameter reiterated at different successive moments on the same drops, preferably a kinetic reaction monitoring within each drop;

for each drop of a plurality of drops, the measuring step comprises measuring several distinct parameters on the same drop;

the internal fluid of each drop comprises a signal reagent, the tagging step comprising a step for optical activation of the signal reagent depending on the classification of the drop;

a plurality of drops are classified during the classification step in a plurality of classes, the tagging step consisting of illuminating each drop from a class with preset illumination conditions, the signal reagent being able to emit a light signal, advantageously fluorescence, after its activation, the drops being sorted based on their light signal level emitted during the recovery step, the level of the light signal emitted by the signal reagent depending on illumination conditions during the activation;

the internal fluid of each drop comprises a signal reagent, the tagging step comprises a step for thermal activation of the signal reagent depending on the classification of the drop;

the emulsion is provided in a two-dimensional chamber, the emulsion being kept in the form of a single layer of drops in the two-dimensional chamber during the measuring step and the tagging step;

a classified drop includes a cell, the tagging step comprising marking the cell, and the selective recovery step comprising an emulsion break followed by sorting by cytometry; and each drop of the emulsion includes a test reagent able to react with an element specific to the drop.

The invention also relates to a system for selecting and recovering products comprising:

a support able to receive an emulsion comprising a plurality of drops contained in a carrier fluid, each drop comprising an internal fluid, a device for measuring at least one physical parameter for several drops of the emulsion received in the support, a classifying unit able to decide the classification of at least one drop of the emulsion based on measurements obtained during the measuring step, a tagging device able to tag a drop or part of the drop based on the classification decision of the drop, and a recovery device of the drop or part of the drop based on the tagging.

The invention will be better understood upon reading the following description, provided solely as an example, and in reference to the appended drawings, in which:

In the following description, the terms "upstream" and "downstream" and the terms "inlet" and "outlet" are used in reference to the normal circulation directions of the fluids of the system. The term "longitudinal" is defined relative to the direction of the circulation conduit in the chip. "Transverse plane" refers to the planes that are perpendicular to the longitudinal direction. The "diameter" of an element refers to the maximum transverse expanse of the considered element in a transverse plane.

In the rest of the description, the term "cell" refers to a eukaryotic or prokaryotic cell. The cells are for example bacteria, yeast, algae, fungi, mammalian cells or the like.

Figure 1:
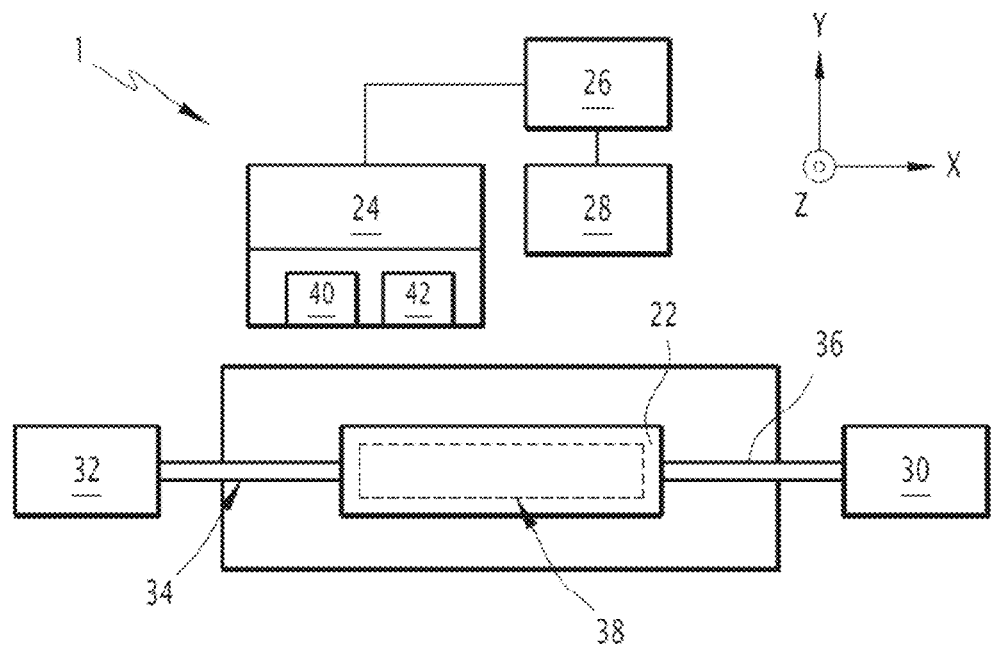
FIG. 1 is a schematic illustration of a system for selecting and recovering products.

A system 1 for selecting and recovering products is shown in FIG. 1. In reference to FIG. 2, the system 1 for recovering drops is provided to analyze the drops 4 of an emulsion 6, and to selectively recover products contained in certain drops 4.

Figure 2:
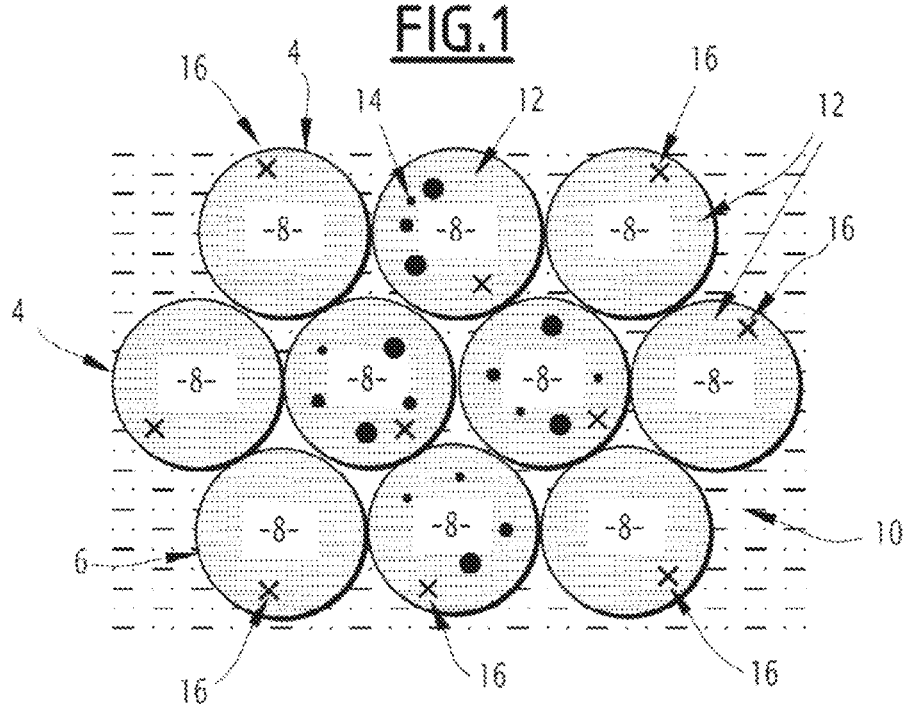
FIG. 2 is a schematic illustration of an emulsion before injection into the drop recovery system.

An emulsion 6 of drops 4 is shown in FIG. 2. The emulsion 6 is made up of a plurality of drops 4 of an internal fluid 8 dispersed in a carrier fluid 10. Each drop 4 makes up a closed compartment filled with internal fluid 8, in which chemical or biological reactions may for example occur that may result in revealing the formation or alteration of a product.

The emulsion 6 is substantially stable, which means that for a fixed volume of the emulsion 6, the number and volume of the drops 4 vary by less than 5% when the fixed volume of the emulsion 6 is kept between −80° C. and 80° C., at 1 bar for 48 hours. The emulsion 6 is concentrated. This means that the volume fraction of drops 4 in the emulsion 6 is between 5% and 99.9%, advantageously between 50% and 80%, in particular equal to 74%. The drops 4 of the emulsion 6 are preferably substantially monodisperse, which means that the polydispersity is less than 5%. The drops 4 for example have a volume comprised between 1 pL and 2 μL. Advantageously, the volume of the drops 4 is comprised between 20 pL and 50 pL, in particular in cell analysis applications.

Thus, the diameter of the drops is generally comprised between 32 micrometers and 46 micrometers.

At least some drops 4 of the emulsion 6 are different from other drops 4 of the emulsion 6. Each drop 4 thus comprises an internal fluid 8 that may be different from one drop 4 to another. Advantageously, the internal fluid 8 of all of the drops 4 comprises at least one same common base 12.

The internal fluid 8 of each drop 4 is made up of elements 14 specific to the drop 4 and the common base 12. The proportions of the specific elements 14 and the common base 12 and/or the natures of the specific elements 14 vary from one drop 4 to the next.

For example, the common base 12 comprises a buffer solution suitable for the survival of cells, such as a phosphate-buffered saline solution or a culture medium. Advantageously, more than 10% of the volume of the drop 4 is made up of the common base 12.

Advantageously, the common base 12 of each drop 4 comprises a signal reagent 16. The signal reagent 16 is present in the same proportions in each drop 4. The signal reagent 16 is able to be activated by a tagging device 28, as will be described later.

For example, the signal reagent 16 is able to emit a fluorescence signal only after it is activated. Advantageously, the intensity of the fluorescence signal emitted by the signal reagent 16 depends on the conditions of the activation.

For example, the signal reagent 16 comprises the CMNB-caged fluorescein (5-carboxymethoxy-2-nitrobenzyl) marketed by ThermoFisher, under the name "Fluorescein bis-(5-carboxymethoxy-2-nitrobenzyl) ether, dipotassium salt (CMNB-caged fluorescein)". This compound is colorless, and non-fluorescent before photolysis. The group forming the cage is able to be lysed under ultraviolet (UV) flashes at 355 nm so as to allow the release of the fluorescein. Fluorescein is a highly fluorescent molecule that can be used for tagging.

The specific elements 14 of a drop 4 are for example chemical or biological reagents able to react with one another, or products of a reaction. For example, the specific elements 14 of a drop 4 are a cell and elements secreted by the cell, such as proteins.

For example, a specific element 14 of certain drops 4 is a fluorescent product with a known excitation and emission length, but the proportions of which are unknown.

In a first example, illustrated by FIGS. 3 and 4, the concentration of a same fluorescent specific element 14, sulforhodamine, varies from one drop 4 to the next, as will be described hereinafter.

The internal fluid 8 of each drop 4 is immiscible with the carrier fluid 10. Immiscible means that the distribution coefficient between the two fluids is less than $10^{-3}$. The drops 4 are well defined in the emulsion 6 and the exchanges between two adjacent drops 4 in the emulsion 6 are limited to the compounds that are soluble or slightly soluble in the carrier fluid 10, i.e., with a distribution coefficient greater than or equal to $10^{-3}$ and in the case where the compositions are different between adjacent drops 4. For example, the internal fluid 8 is an aqueous phase and the carrier fluid 10 is an organic phase, in particular an oily phase. The carrier fluid 10 for example comprises hydrofluoroethers such as FC-40 or HFE-7500, forming a fluorinated oil.

The carrier fluid 10 further advantageously comprises a surfactant. The surfactant is able to stabilize the emulsion 6. The surfactant is for example a block copolymer of polyethylene glycol and perfluoropolyether (PEG-PFPE), Krytox-Di-PEG obtained by Ran Biotechnolgies or QX200™ Droplet Generation Oil with surfactant obtained by BioRad. For example, the surfactant concentration in the carrier fluid 10 is between 2% and 5%.

As illustrated in FIG. 1, the system 1 comprises a support 20 defining a chamber 22 for receiving an emulsion 6. The system 1 further comprises a device 24 for measuring at least one physical parameter for several drops 4 of the emulsion 6 received in the support 20, a classification unit 26, a tagging device 28, and a recovery device 30.

The emulsion 6 is for example prepared by a preparation device. It is stored before being placed in the chamber of the system 1 by an injection module 32 for injecting the emulsion. For example, the injection module 32 comprises a syringe pump, a piezoelectric device or a pressure-based flow controller.

For example, the support 20 is a chip. The chip 20 is, in the example, a rectangular block extended along the longitudinal axis X and a transverse axis Y perpendicular to the longitudinal axis X. Furthermore, the chip has a thickness along an elevation axis Z perpendicular to the longitudinal axis X and the transverse axis Y. The chip 20 comprises an inlet conduit 34, the chamber 22 and an outlet conduit 36. The inlet conduit 34 is able to be placed in fluid communication upstream with the injection module 32 for injecting the emulsion. The outlet conduit 36 is able to be placed in fluid communication downstream with the recovery device 30, as illustrated in FIG. 1.

The chamber 22 is intended to store a plurality of drops 4 in the carrier fluid 10 during a measuring and tagging step. The chamber 22 advantageously has dimensions adapted to the dimensions of the emulsion 6 to be studied in order for the drops 4 to be distributed in the chamber after a step for loading the emulsion 6. The drops 4 are advantageously distributed in a two-dimensional layer along the plane of the chip comprising the longitudinal axis X and the transverse axis Y. No drop 4 is superimposed on another drop 4.

For example, the drops 4 are spherical in the chamber 22 and the height of the chamber 22 along the axis Z is substantially equal to the diameter of a drop 4. Alternatively, the height of the chamber 22 is smaller than the diameter of the drops 4 of the emulsion 6 and the drops 4 are in the shape of flattened pucks along the axis Z in the chamber 22.

The chamber 22 has a measuring region 38. The measuring region 38 is able to contain between 1,000 drops and 10,000,000 drops of the emulsion at the same time, in particular $10^5$ drops. Furthermore, the dimensions of the measuring region 38 are suitable for it to be able to be completely swept by the measuring device 24 and the tagging device 28.

The chip 20 is transparent at least in the measuring region 38 to allow the measurement of a physical parameter over the drops 4 present in the measuring region 38 by the measuring device 24.

Advantageously, the chip 20 is made from a transparent material, for example glass or transparent plastics such as polydimethylsiloxane (PDMS), polymethyl methacrylate (PMMA), cycloolefin copolymers (COC) or the like. The material of the chip 20 is advantageously impermeable to the carrier fluid 10.

Successively or simultaneously, the measuring device 24 is able to measure at least one physical parameter for several drops 4 of the emulsion 6 received in the support 20. Advantageously, it is able to measure the parameter for all of the drops 4 present in the measuring region 38.

The measuring device 24 in particular allows an optical measurement of the drops 4.

For example, the measuring device 24 comprises a sensor 40 able to detect the light coming from a drop 4 of the measuring region 38 and a light source 42.

For example, the sensor 40 is a CCD camera able to form an image of the measuring region 38. The obtained image resolution for example makes it possible to identify cell types present in the drops 4 using morphological criteria.

The light source is for example able to selectively illuminate a drop 4 without illuminating the adjacent drop 4.

Alternatively or additionally, the light source 42 is able to illuminate the measuring zone 38 completely.

For example, the light source 42 is a white light source arranged to illuminate the drops 4 of the measuring region 38. Alternatively or additionally, the light source 42 comprises an excitation laser or a fluorescent lamp arranged to emit radiation over the measuring region 38.

Advantageously, the sensor 40 and the source 42 of the measuring device 24 allow measurements on several fluorescence channels, on the scale of each drop. For example, the following combinations were used for the measuring device 24: a GFP filter assembly (excitation 465-495 nm, dichroic 505 nm, emission 515-555 nm), a TRITC filter (excitation 530-560 nm, dichroic 570 nm, emission 590-650 nm) and Cy5 filter (excitation 600-650 nm, dichroic 665 nm, emission 670-725 nm). Each fluorescence channel can be used to measure different characteristics.

The measuring device 24 is for example a two-dimensional scanning device as described in document WO 2010/007307 A2.

Furthermore, the measuring device 24 is able to communicate the obtained measurements to the classification unit 26.

The classification unit 26 is able to receive the signals from the measuring device 24 and process them and record the characteristics of the drops 4. For example, the classification unit 26 includes a memory and a microprocessor. The classification unit 26 is able to decide the classification of at least one drop 4 of the emulsion 6 based on measurements obtained during the measuring step.

Classification criteria are for example recorded in the memory. Alternatively or additionally, the memory is able to record successive measurements done at different moments by the measuring device 24, for example, for kinetic reaction monitoring within several drops 4. The microprocessor is able to perform calculations from measurements and compare the results of the calculations to parameters of the classification criteria.

Advantageously, the classification unit 26 includes a man-machine interface in order for a user to be able to recover the results obtained during the measuring step and adjust the classification criteria based on these wishes or results obtained during the measuring step.

The tagging device 28 is able to tag a drop 4 or part of the drop 4 based on the classification decision of the drop 4.

For example, the tagging device 28 comprises a laser able to specifically illuminate a drop 4 with preset parameters so as to activate the signal reagent 16.

In one example, two separate light sources are used for the tagging device 28 and for the measuring device 24.

In one alternative, the same light source 42 is used both for the measuring device 24 and for the tagging device 28. For example, during the measuring step, the light source 42 illuminates the entire measuring region 38 to have a significant reading flow rate. However, during the tagging step, the light source 42 illuminates the drops 4 selectively so as not to tag two adjacent drops 4.

Alternatively, the tagging device 28 comprises a source able to specifically heat a drop 4 with preset parameters so as to activate the signal reagent 16.

Alternatively, the tagging device 28 comprises an electrode circuit able to generate an electrical field in one drop specifically, with preset parameters, so as to activate the signal reagent 16 by heating, or to perform selective lysis of a cell or a lysosome.

The injection module 32 is for example able to cause the emulsion 6 to exit through the outlet conduit of the chamber 20 so that it is injected into the recovery device 30.

The recovery device 30 is able to allow a drop 4 or part of the drop to be recovered based on the tagging. For example, the recovery device 30 allows the entire drop 4 to be recovered. Alternatively, the recovery device 30 allows a cell of the drop 4 to be recovered. For example, the recovery device 30 comprises a flow cytometer or a sorting device. One sorting device used, for example, is that described in the article "Single-cell analysis and sorting using droplet-based microfluidics", published in 2013 in Nature Protocols vol 8,870-891.

The recovery device 30 is advantageously able to measure a cell corresponding to the activated signal reagent 16 and to perform sorting based on said signal.

A first method for selecting and recovering products will now be described. The selection and recovery system 1 previously described is provided for carrying out said method.

The module 32 for injecting the emulsion 6 is provided with an emulsion 6 as previously described. The emulsion 6 of drops 4 is injected into the chamber 22 using the injection device for injecting the emulsion 6. Alternatively, the system 1 is provided directly with the emulsion 6 in the chamber 22.

Advantageously, in the chamber 22, the drops 4 are arranged according to a compact arrangement, in particular an arrangement in staggered rows along a plane transverse to the axis Z at least in the measuring region 38.

During a measuring step, a physical parameter is measured for several drops 4 of the emulsion 6 present in the measuring region 38.

The measuring step is performed in the chamber 22 with no circulation of the drops 4. The spatial location 6 of each drop is recorded at the same time as these parameters in the memory of the classification device 26.

During the measuring step, the fluorescence signal of the drop 4 for a given excitation wavelength, and a given emission wavelength, is measured by the measuring device 24.

For example, said wavelength corresponds to the wavelength of a desired product.

Following the measuring step, the classification device 26 decides on the classification of the drops 4 based on the obtained measurements.

For example, during this classification step, the results are analyzed and compared to one another and to the classification criteria. The classification device 26 determines to which class at least one drop 4 belongs.

During the classification, for example, all of the drops 4 having an intensity, in the fluorescence channel of the desired product, above a certain threshold are assigned to the same class. The threshold is for example determined relative to the average intensity of all of the drops 4 of the emulsion 6.

The classification is advantageously automated. Alternatively, the classification is done by an operator using a man-machine interface.

The drops 4 are next tagged using the tagging device 28 based on their class.

Advantageously, the drops 4 are kept immobile in the chamber 22, for the time needed for the measuring and tagging steps.

The tagging for example comprises a step for illuminating the drops 4 to activate the signal reagent 16 optically. The illumination is for example done by a laser of the tagging device 28.

After the tagging step, a recovery step is carried out. The recovery step comprises a step for transferring drops 4 or their contents into the recovery device 30. For example, the emulsion 6 is injected into the recovery device using the injection module 32.

After the tagging, the drops 4 that have been classified, then tagged can be distinguished from the other drops, based on their marking. Thus, even if the spatial distribution of the drops 4 is modified, for example during their collection or transfer to the recovery device 30, it is possible to determine their class.

After the transfer, a measuring step is advantageously carried out by the recovery device 30 and all of the drops 4 having a signal from the signal reagent 16 above a detection threshold are collected in a same tube. The signal from the activated signal reagent 16 makes it possible to recover these drops 4 specifically during a recovery step. The drops 4 are sorted based on their tagging.

Such a system thus makes it possible to separate the emulsion 6 into at least two populations of drops and allows the specific recovery of a population of drops 4.

Keeping the drops 4 in the measuring zone 38 during the measuring and tagging steps makes it possible to obtain a fine and precise characterization of the tagged drops 4. Furthermore, the measuring step can be longer than in flow cytometry systems. The measuring may for example be reiterated. Several measurements may thus be integrated per drop 4 before performing the classification step. This avoids selecting a drop 4 based on a single measurement that may be noised. The classified drops 4 are thus better characterized before recovery thereof.

Furthermore, the recovery is based on the tagging signal and not the measurement signal. It is possible to effectively isolate a class of drops 4 that have measured characteristics close to the other drops 4 by precisely adjusting the classification criteria before tagging.

A first example implementation of the first method will now be described in light of FIGS. 3 and 4. In this example, the emulsion 6 is formed from three emulsions comprising drops comprising different concentrations of sulforhodamine. Each drop 4 of each emulsion further comprises the same proportion of the signal reagent 16, which is CMNB-caged fluorescein.

The concentration of the signal reagent 16 used for the tagging is for example comprised between 1 nM and 100 µM, and advantageously equal to 2 µM.

During the measuring step, the fluorescence signal corresponding to the sulforhodamine is recorded for several drops 4 of the measuring region 38. FIG. 3 shows part of the measuring region 38 observed in the fluorescence channel corresponding to the sulforhodamine. In this figure, it is possible to distinguish three types of drops 4 respectively having a low intensity 60, a medium intensity 62 or a high intensity 64 of the fluorescence signal. Each type of drop 60, 62, 64 in this example comes from an emulsion with a different sulforhodamine concentration. The drops 64 having the highest intensity of the drops 4 comprising the highest concentration of sulforhodamine.

During the classification, the medium intensity of all of the drops 4 of the emulsion is calculated. An intensity threshold is calculated as for example being 1.5 times this medium value. All of the drops 4 having an intensity, in the fluorescence channel of the desired product, above this threshold are assigned to a first class. These drops 4 classified in the first class correspond to the drops 64 with a high intensity in FIG. 3.

During the tagging step, the drops 64 belonging to the first class are illuminated selectively by a UV flash, at 355 nm, having a duration of 5 seconds. With these flashes, the CMNB cages are cleaved and the fluorescein is released. The signal reagent 16 of these drops 4 is thus activated.

Figure 3:
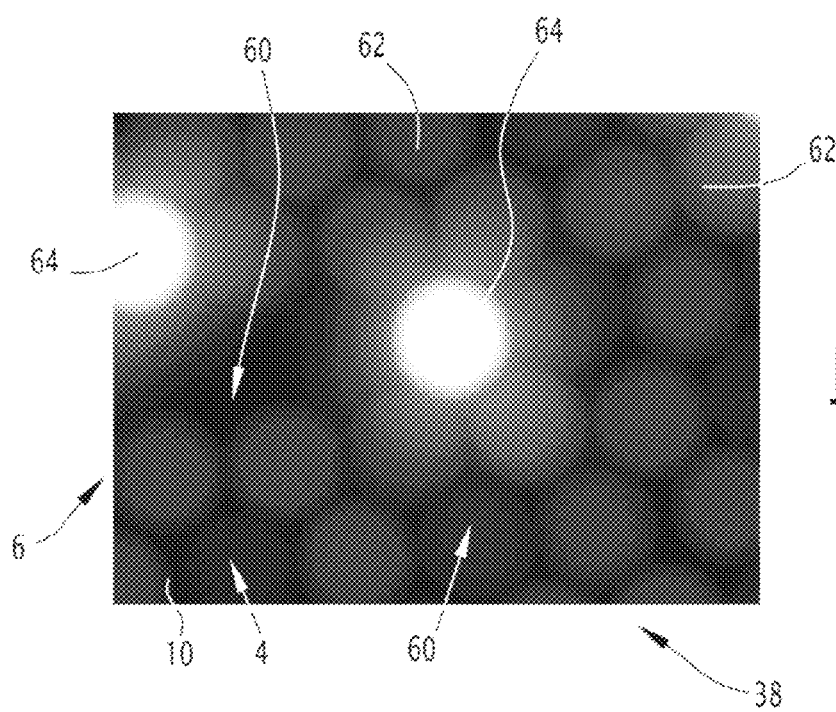
FIGS. 3 to 4 illustrate a first example application of the system for selecting and recovering products.
Figure 4:
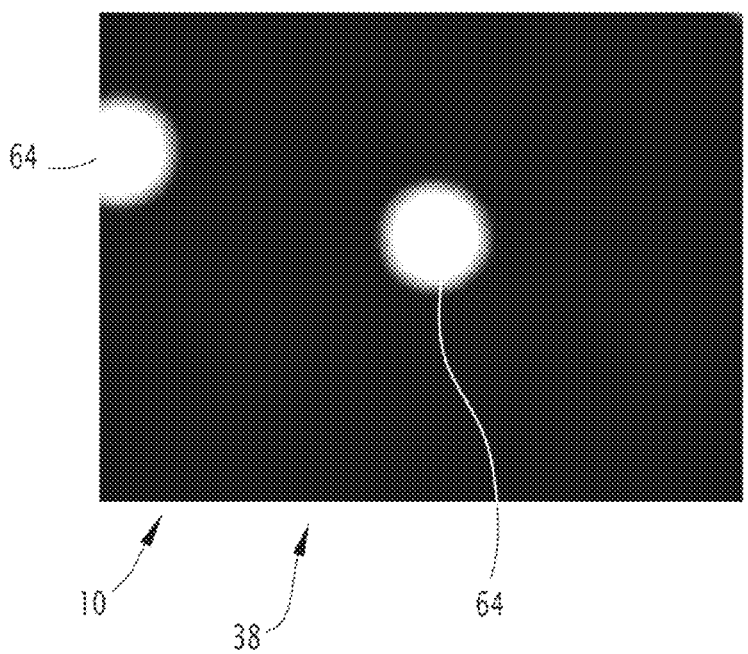

FIG. 4 shows the same part of the measuring region 38 as FIG. 3, after the tagging step, observed in the fluorescence channel corresponding to the fluorescein. Only the drops 64 that have a high intensity in FIG. 3 have been marked during the tagging step. They thus have a significant intensity in the fluorescein channel. The contrast is significant, since the other drops 60, 62, not classified, have not been illuminated by the UV flashes, their signal reagent 16 has not been activated, they are therefore not fluorescent in the fluorescence channel of the fluorescein. This figure shows that the classified drops 64 have been tagged, but not the others.

During the recovery step, the drops 4 are sorted based on their fluorescence signal in a channel corresponding to the fluorescein by the recovery device 30. The drops 64 that had a high sulforhodamine concentration are thus isolated from the other drops 60, 62 of the emulsion 6 based on a tagging signal with a high contrast. They can thus be recovered quickly and efficiently.

A second method for selecting and recovering products will now be described. This method differs from the first method in that during the classification step, a plurality of drops 4 are classified during the classification step in a plurality of classes.

During the tagging step, each drop 4 of a class is illuminated with preset illumination conditions, the level of the fluorescence signal emitted by the signal reagent 16 depending on the illumination conditions during the activation. The drops 4 are next sorted based on their fluorescence level during the recovery step.

In a second example, the second method is implemented. The second example is identical to the first example until the classification step. During the classification step, two thresholds are determined. A first intensity threshold is calculated as being 1.5 times this average value, and a second threshold is calculated as being 0.5 times the average value. All of the drops having an intensity above the first threshold are assigned to a first class, and all of the drops having an intensity below the second threshold are assigned to a second class.

Figure 5:
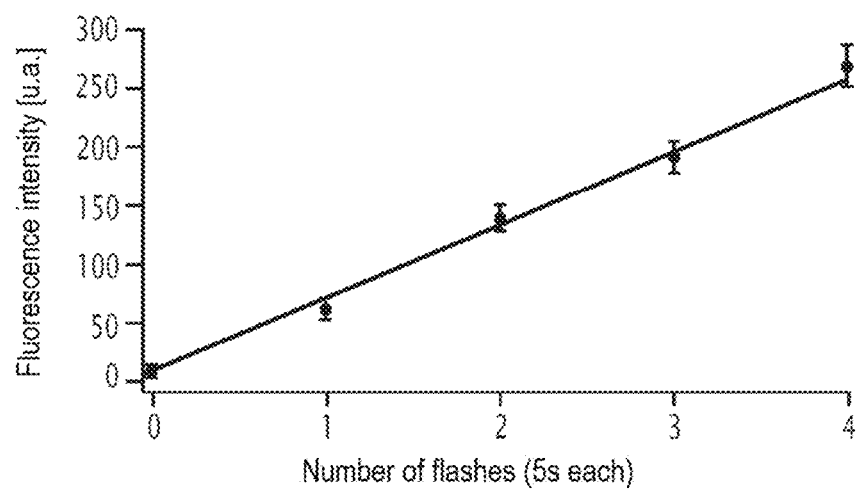
FIG. 5 illustrates a second example application of the system for selecting and recovering products.

Several fluorescence levels can be reached from the same quantity of CMNB-caged fluorescein, by modifying the number of UV flashes sent on a drop 4, as shown on the graph of FIG. 5. This makes it possible to modify the tagging signal based on the classes of the drop 4. Thus, the drops 64 of the first class are illuminated with one flash.

The drops 60 of the second class are illuminated with four flashes.

After the tagging step, the drops 60 of the second class have a high intensity in the fluorescein channel and the drops 64 have an intensity in the fluorescein channel that is lower, but easy to detect. The drops 62 that have not been classified are not fluorescent in the fluorescein channel.

During the recovery step, the drops 64 that comprise a high sulforhodamine concentration are thus isolated. Likewise, the drops 60 that comprise a low sulforhodamine concentration are isolated based on a tagging signal with a high contrast. Each category can thus be recovered effectively.

A third method for selecting and recovering products will now be described. This method differs from the first method and the second method in that the common base 12 of each drop 4 further comprises one or several test reagents.

The test reagents make it possible to measure physical parameters in the drop 4. Each test reagent is present in the same proportions in each drop 4 of an emulsion 6.

For example, the test reagents are the reagents necessary to carry out an ELISA test in a drop or are the reagents of an immunological test.

Advantageously, at least one test reagent or a product of the test reactions is fluorescent. Measurements are then done by the measuring device 24 on different fluorescence channels corresponding to the different reagents or fluorescent products.

The signal reagent 16 is advantageously chosen so as not to intersect the fluorescence channels of the reagents or test products.

During the measuring step, the efficacy of the specific elements 14 of the drops is tested and measured by the tests.

Advantageously, the measuring step comprises measuring a characteristic parameter of the test, reiterated at different successive moments. Reiterating the measurement makes it possible to perform kinetic monitoring of the test reaction within the drops 4.

Figure 6:
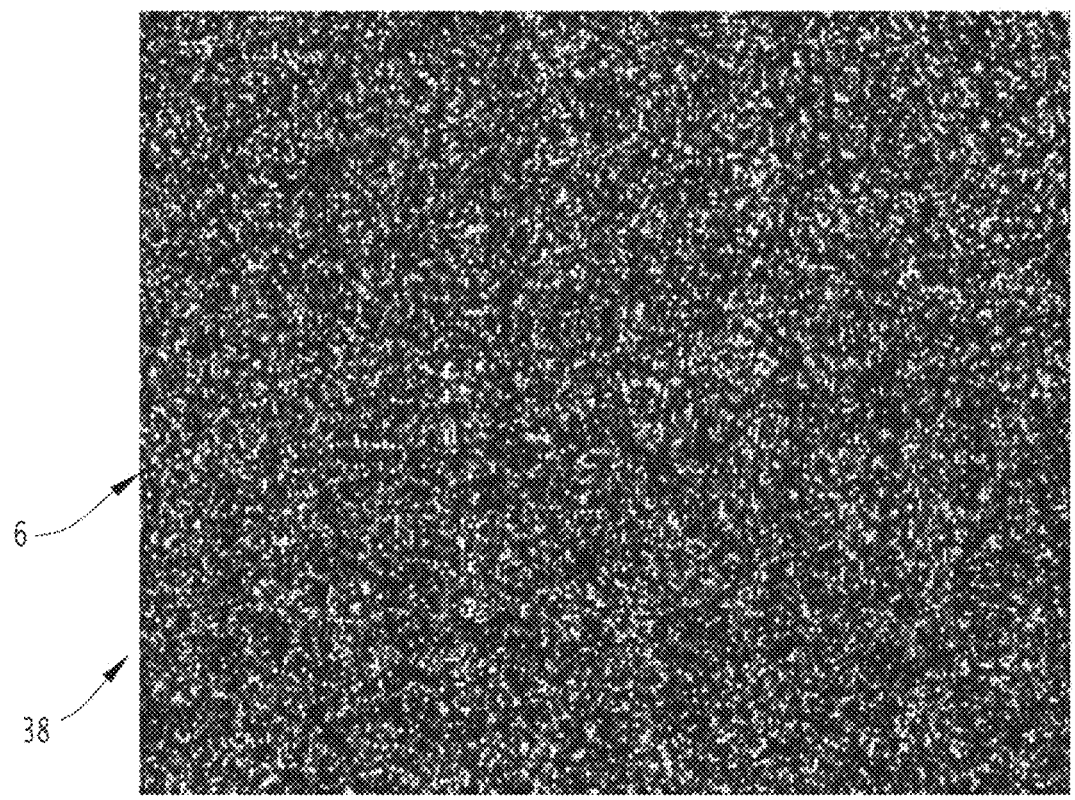
FIG. 6 illustrates a third example application of the system for selecting and recovering products.

In the third example shown in FIG. 6, the measuring region 38 has a length of 10 mm and a width of 8 mm and comprises 40,000 drops. The different points each correspond to a drop and the different gray levels correspond to different fluorescence intensities in an excitation channel corresponding to a test reagent. The duration of the measuring step depends on the tests done. In the example of FIG. 6, a measurement on four different fluorescence channels for 40,000 drops lasts about 10 minutes.

Once the measurements are done, it is possible to perform a classification of the drops based on the results. The classification thus pertains to several measured parameters. The drops 4 can thus be classified based on the results of the tests. For example, the drops 4 are classified based on the yields of the reactions that take place in the drops 4 and the speeds of said reactions.

For example, the drops 4 that have a good result in the affinity test with an antigen are identified during the classification step. They are classified in a class associated with their result in the test.

Tagging these drops makes it possible to separate them easily from the others using a traditional sorter. The drops can thus be recovered easily with tagging signals corresponding to their category.

This method allows simple recovery of the drops, since it is done on a single parameter, whereas selecting them is complex and based on several parameters. Since recovery is simple, the recovered drops can be analyzed downstream using other methods. For example, if the drops contain cells, they can be sequenced or put back in a culture.

Figure 7:
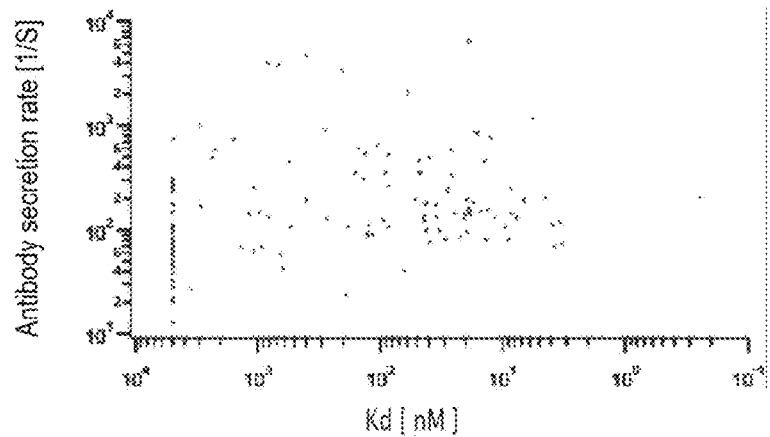
FIG. 7 illustrates a fourth example application of the system for selecting and recovering products.

A fourth example illustrating the implementation of the third method will now be described in light of FIG. 7. In this example, the aim is to identify and isolate cells producing an antibody reacting against an antigen of *the Tetanus Toxoid* (TT) protein.

An emulsion 6 comprising 40 pL drops and comprising zero or one antibody-producing cell is formed. Each drop comprises reagents allowing the phenotypical characterization of the produced antibodies, in particular of the TT test reagents. Furthermore, each drop 4 comprises a photo-activated marker, such as caged fluorescein.

The drops 4 are arranged in the chamber 22 according to a two-dimensional array suitable for each drop 4 of the measuring zone 38 to be able to be illuminated and viewed separately.

During the measuring step, the affinity in the number of antibodies is measured. FIG. 7 shows, for each drop 4, the antibody secretion rate based on the measured affinity of the antibodies. In this graph, each point corresponds to a drop 4. Such a graph is for example displayed on the classification device 26 to allow the user to choose the classification criteria.

In this example, 15,000 drops are present in the measuring region 38; 12,000 drops comprise cells. Among these 12,000 drops, only 200 drops have antibodies acting against TT in a detectable quantity, only 21 of which have a high affinity. These 21 drops are placed in a first class to be recovered. Advantageously, the other drops comprising antibodies with a low affinity are classified in a second class to be used for comparison. Furthermore, several drops comprising cells not having generated antibodies and several drops not comprising cells are classified in a third class and a fourth class to be used subsequently as blank or negative control in other experiments making it possible to characterize the cells.

The illumination of a classified drop makes it possible to activate the photo-activated marker specifically in said drop, the adjacent drops 4 not being illuminated. During the tagging step, the selected drops 4 are illuminated one by one with parameters corresponding to their class.

During the recovery step, the drops 4 comprising the most antibodies or the best antibodies are selectively recovered in a tube, and the cells having secreted said antibodies can be placed back in culture. Alternatively, after the recovery, the cells are lysed and their DNA or their RNA is amplified and sequenced using known techniques.

The system makes it possible not to drown these cells, of which there are few, in measuring noise related to the large number of cells in other classes.

A fourth method for selecting and recovering products will now be described. The signal reagent 16 comprises a cell marker to be activated. The classified drops comprise a cell. The cell marker, once activated, is able to attach itself and mark the membrane of the cells present in the classified drop. For example, the activated cell marker fixed to the membrane is fluorescent.

The tagging step comprises marking the cell, and the selective recovery step comprises an emulsion break followed by sorting by cytometry.

For example, the marking of the cell is membrane, intracellular, or at the cellular organelles, such as the lysosomes.

Such a signal makes it possible to specifically recover the tagged cells during a recovery step. During this recovery step, the emulsion 6 is broken such that the internal phases 8 of the drops 4 fuse and form a continuous phase. The continuous phase is recovered. Sorting by cytometry of the continuous phase, for example in a cell sorter by fluorescence, makes it possible to isolate the marked cells. The cells of the continuous phase are sorted based on their marking done during the tagging step.

Such a method allows the specific recovery of a cell after a complex measurement of its phenotyping for many cells.

A fifth example illustrating the implementation of the fourth method will now be described. In this example, the aim is to tag the cells directly during the tagging step before they are recovered by breaking the emulsion.

For example, before the introduction into the drops, the cells are marked with a nonfluorescent reagent that reacts with an element of the accessible membrane, such as amine groups present in the proteins and certain lipids. The most favorable reagent is activated by light, and in this process, becomes fluorescent. The reagent is for example CMND-caged carboxyfluorescein, SE (5-Carboxyfluorescein-Bis-(5-Carboxymethoxy-2-Nitrobenzyl) Ether, β-Alanine-Carboxamide, Succinimidyl Ester) marketed by ThermoFisher. Activation using UV light yields fluorescent cells sortable after recovery of the drops and cells.

Alternatively, the cells are marked before the experiment with sulfo-SBED (Sulfo-N-hydroxysuccinimidyl-2-(6-[biotinamido]-2-(p-azido-benzamido)-exanoamido) ethyl-1,3'-dithioproprionate, Thermo Fisher 33033). This complex comprises three reaction groups: a Sulfo-N-hydroxysuccinimidyl ester capable of reacting with primary amine groups, a photo-activated group (azido-benzamide group) and a biotin molecule. This marker is added to all of the cells before the experiment. It reacts with the amine groups of the cell membrane, present in proteins or membrane lipids.

An emulsion 6 comprising 40 pL drops and comprising zero or one of these cells functionalized with sulfo-SBED is formed. The drops are arranged in the chamber 22 like before.

After the measuring step and the classification step, the cells of the selected drops are illuminated by the UV light.

The UV light activates the azido-benzamide group, which reacts with the cell membrane forming a molecule attached by two chemical groups to the cell surface. After tagging, the drops are recovered and the emulsion is broken.

A centrifugation step makes it possible to purify the cells. Recovering all of the cells makes it easier to manipulate the cells and results in less loss of the cells of interest.

Lastly, the cells are set to incubate in a solution comprising a reducing agent, such as di-thiotreitol (DTT) at 25 mM. This makes it possible to cleave the hydroxysuccinimidyl chains that bond the disulfide group to the biotin. Thus, the biotin is removed from all of the cells that have not been activated by the UV rays during the tagging step. In the tagged cells, the bond of the disulfide group is also cleaved, but the activated azido-benzamide holds the biotin to the cell membrane.

As a result, only the cells illuminated during the tagging step have biotin molecules on their membrane.

The biotin can next be marked by fluorescent streptavidin, such as streptavidin-Alexa555, marketed by ThermoFisher. The marked cells are thus highly fluorescent relative to the rest of the cell population. The cells can next be recovered by FACS.

Alternatively, the biotinylated cells are bonded to functionalized magnetic beads with streptavidin. The cells are next purified by removing them from the solution magnetically.

Alternatively, before forming the emulsion, the cells are functionalized with another activatable membrane marker having a fluorescein group or a particular chemical group such as azide, biotin, NTA or the like.

In one alternative, the signal reagent 16 comprises primers or reagents allowing marking of the DNA or RNA to be activated, for example messenger RNA marking. Furthermore, the cells are for example lysed in the respective drops 4.

This signal reagent 16, once activated, is able to mark the DNA or the messenger RNA present in the selected drop 4, for example using a fluorescent signal.

Alternatively, the DNA or RNA of interest is marked by a chemical group such as an azide, an alkyne, chelators such as nitrilotriacetic acid (NTA), or magnetic particles. Such marking makes it possible to specifically recover the tagged DNA, RNA or mRNA during a recovery step. During this recovery step, the emulsion is broken such that the internal phases of the drops form a single continuous phase.

The marked DNA or RNA are purified using an appropriate purification method for the signal reagent 16 used. For example, they are recovered by click chemistry for the azides or alkynes, by Nickel resin purification for NTA.

Such a technique for example facilitates the sequencing of interesting mRNA.

In one alternative, the drop 4 does not comprise signal reagent 16. The tagging step consists of performing laser lysis of the cells of classified drops 4. During the recovery step, the emulsion 6 is broken, and the products are purified by centrifugation. The non-lysed cells and the debris are removed. This allows specific recovery of the cytoplasms of the selected cells.

One alternative consists of lysing all of the cells of the unmarked drops. During the recovery step, the emulsion 6 is broken, the lysed cells and the debris are removed. This allows specific recovery of the selected cells.

In one alternative, the activation of the signal reagent 16 increases its density. During the tagging step, the density of the classified drop 4 is increased. During the recovery step, the emulsion is injected without being broken into a device allowing the separation by density, for example in a decanting flask. This allows a recovery of the classified drops 4.

In one alternative, the signal reagent 16 is able to be activated under local heating conditions. The local heating is used for the lysis of cells or liposomes. The considered liposomes release a molecule, advantageously which makes it possible to mark the drop or the cell after the release. This released molecule can cause fluorescent marking of the cell or the drop or change the nature of the cell.

The tagging step comprises a step for thermal activation of the signal reagent 16 depending on the classification of the drop 4. During the tagging step, the selected drops are heated locally using the tagging device.

A fifth method will now be described. This method is implemented in the fifth example shown in FIGS. 8 and 9.

This method differs from the methods previously cited in that the drops comprise at least one clump of particles defining an object elongated along a main axis, at least some drops containing at least one target element able to attach on the clump, the measuring step comprising measuring a characteristic physical parameter of the bonding of the target element on the clump.

Figure 8:
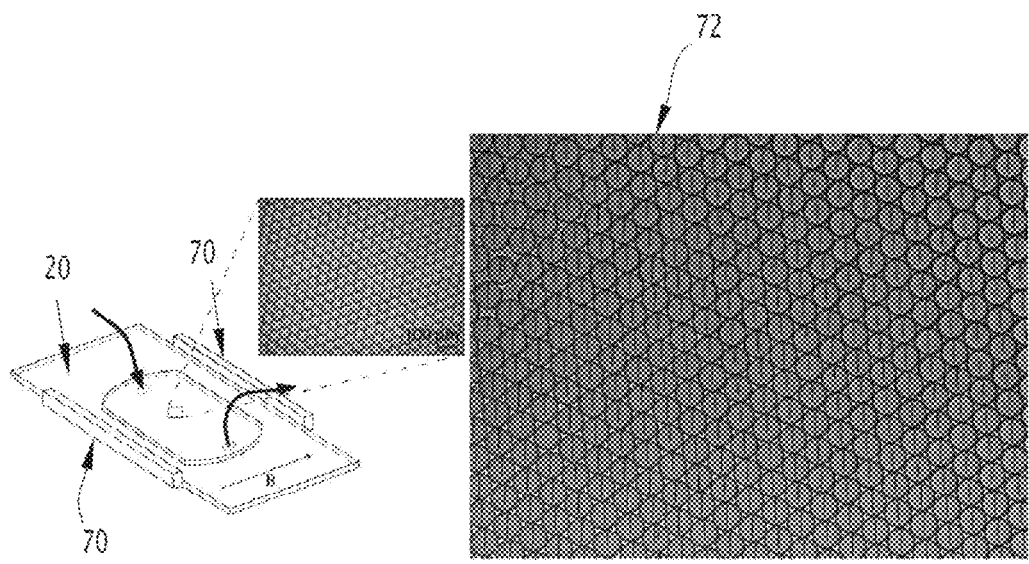
FIGS. 8 to 9 illustrate a fifth example application of the system for selecting and recovering products.

The support 20, as illustrated in FIG. 8, comprises supply devices 70 able to form a magnetic field B so that the particles form an elongate clump 72.

The particles are superparamagnetic particles. The particles are able to form an elongate clump 72 in the form of a column when a magnetic field is applied. The measurement of the characteristic physical parameter of the bonding of the target element on the clump is done locally in a plurality of points located in the drop, the measuring step preferably including determining the integral of the values measured within the drop. During the measuring step, the particles are organized to form the elongate clump 72 in a column. This system makes it possible to obtain fluorescence measurements with a better contrast for kinetic monitoring.

The fifth example illustrates the possibility of simultaneously measuring the secretion kinetics and the affinity for a given antigen, of monoclonal antibodies generated by isolated unique primary cells in drops during the measuring step. The unique element 14 allowing the selection of the drop 4 is a monoclonal antibody secreted by a primary cell. This secretion is measured kinetically.

In this example, the drops have a volume of 40 picoliters. In this example, the cells to be analyzed and classified are B lymphocytes extracted beforehand from the spleen of a mouse and purified using a standard procedure (Pan B kit II #130-104-443, Miltenyi Biotec).

The test reagents comprise an antigen, a quantifying entity and particles capable of forming a clump 72 and having a capture entity. The antigen is able to form a complex with the desired antibody. The quantifying entity is also able to form a complex with the antibody.

The antigen is a fluorescent antigen, more specifically "TT-AF488", the *Tetanus Toxoid* protein functionalized beforehand with an AlexaFluor-488 fluorophore, owing to a marking procedure of a standard kit, for example provided by ThermoFisher. Each drop comprises 25 nM of TT-AF488. The magnetic particles used to form the columns of drops are marked to saturation with a capture entity, here the "CaptureSelect™ Biotin Anti-LC-kappa (Murine) conjugate" (ThermoFisher #7103152500). These particles are Streptavidin magnetic particles (Ademtech #0433), marked to saturation with the capture entity. In the example, the quantifying entity used is Rabbit Fab 2 anti-FCmouse AF647, JacksonIR #315-606-146. Each drop comprises 75 nM of this quantifying entity.

The ratio of the fluorescence signal of the antigen to the fluorescence signal of the quantifying entity is correlated to the dissociation constant of the antibody. The dissociation constant Kd is evaluated from the fluorescent antigen concentration measurement related to the antibody immobilized on the bead column and the simultaneous measurement of the antibody concentration captured on the bead column.

Figure 9:
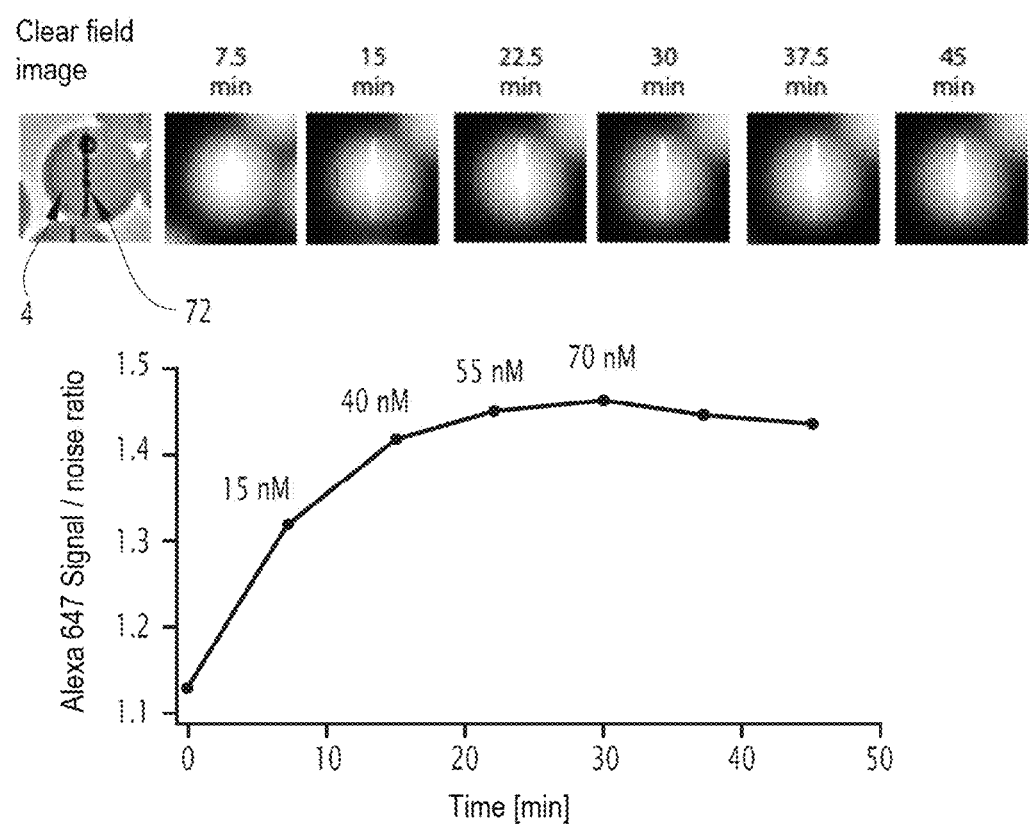

FIG. 9 is a graph showing the evolution, on the scale of a single cell, of the ratio of the relocalized signal of the line of magnetic beads to the dispersed signal of the drop as a function of time (in minutes). "Relocalized signal" refers to the fluorescence signal near the clump, and "dispersed signal" refers to the fluorescence signal in the rest of the drop.

Furthermore, owing to a titration curve, it is possible to correlate the measured signal with a concentration of monoclonal antibodies. This concentration is noted in FIG. 9. The titration curves are for example done with the measuring device 24 from emulsions comprising a known quantity of anti-TT antibodies, called TT7. The TT7 used to produce titration curves was obtained by recombinant protein expression from the sequence published in the article published in the article written by Brandon J DeKosky et al., titled "High-throughput sequencing of the paired human immunoglobulin heavy and light chain repertoire", which appeared in Nature Biotechnology Volume:31, pages 166 to 169 in 2013.

The method for selecting and recovering products according to the invention is more reliable and faster than the existing methods, and allows a precise characterization and efficient recovery of the content of interest of a drop.

One advantage of the method is that it makes it possible to take kinetic measurements before the recovery. This makes it possible to monitor the biological response to stimuli and makes it possible to calculate different parameters. Furthermore, being able to take several measurements makes it possible to better distinguish false positives from positives during a test.

This system 1 is useful to study the cell systems at the single-cell level. Furthermore, this system allows a selection based on complex phenotypes. For example, interactions between cells and bacteria can be observed during the measuring step. This would make it possible to classify and recover the cells in different groups based on their behavior with respect to the bacteria. Likewise, interactions between different cells present in a same drop can be observed during the measuring step.

The system 1 makes it possible to characterize cell secretions by drop. The analyzed cell secretions can be antibody, cytokine and hormone secretions. If the drop comprises a cell, the secretions in the drop correspond to that cell. As a result, it is highly advantageous to be able to measure parameters of the secretions and to recover the entire drop or the cell having led to said secretions. Such a system makes it possible to conduct in vivo studies of antibody-producing cells while allowing a functional characterization of their phenotype on the one hand, in particular through a determination of bonding coefficients, the affinity and the specificity of the secreted antibodies with a target antigen, and a recovery of the cells on the other hand. The recovery for example allows studies of the genotype of the selected cells. Selecting the cells based on their phenotype avoids having to sequence the cells whose phenotype is not of interest and makes it possible to find the genetic sequences of interest more easily. Indeed, the correlations are easier to make and the measuring noise is reduced.

Figure 10:
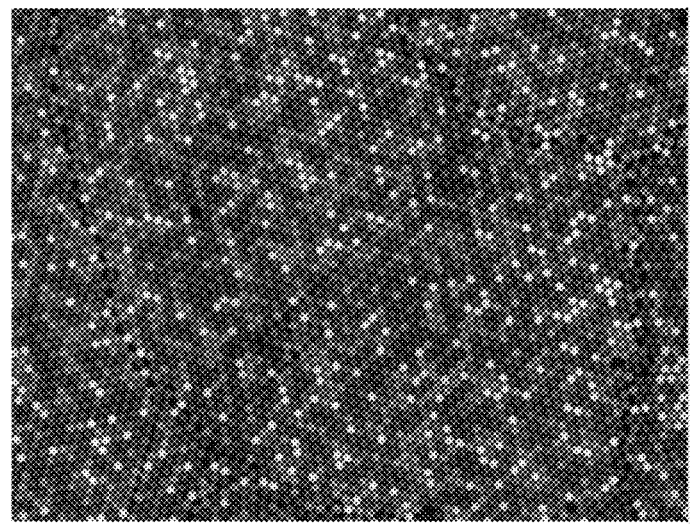
FIGS. 10 to 11 illustrate a sixth example application of the system for selecting and recovering products.
Figure 11:
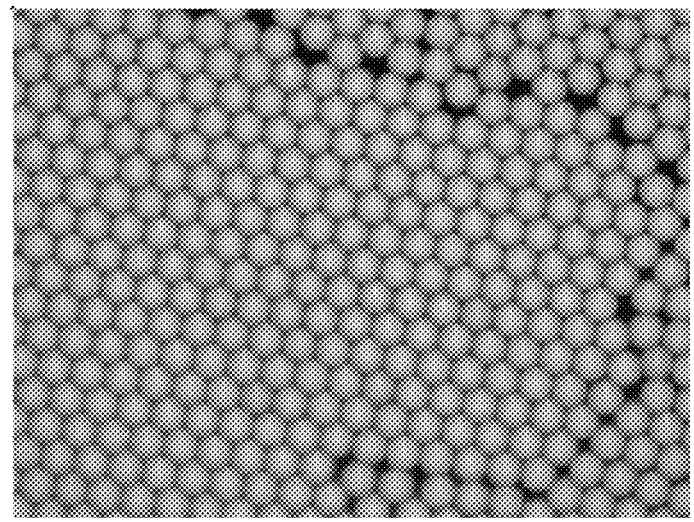

FIGS. 10 to 11 illustrate a sixth example application of the system for selecting and recovering products. This sixth example is similar to the first example.

FIG. 10 shows an emulsion 6 formed from drops comprising different concentrations of sulforhodamine before the selection using the method according to the invention.

In this example, only the drops comprising a concentration of sulforhodamine of 200 nM are tagged by releasing caged fluorescein. Only the tagged drops are next recovered.

FIG. 11 illustrates an image of the recovered drops. These drops have substantially the same intensity.

Figure 12:
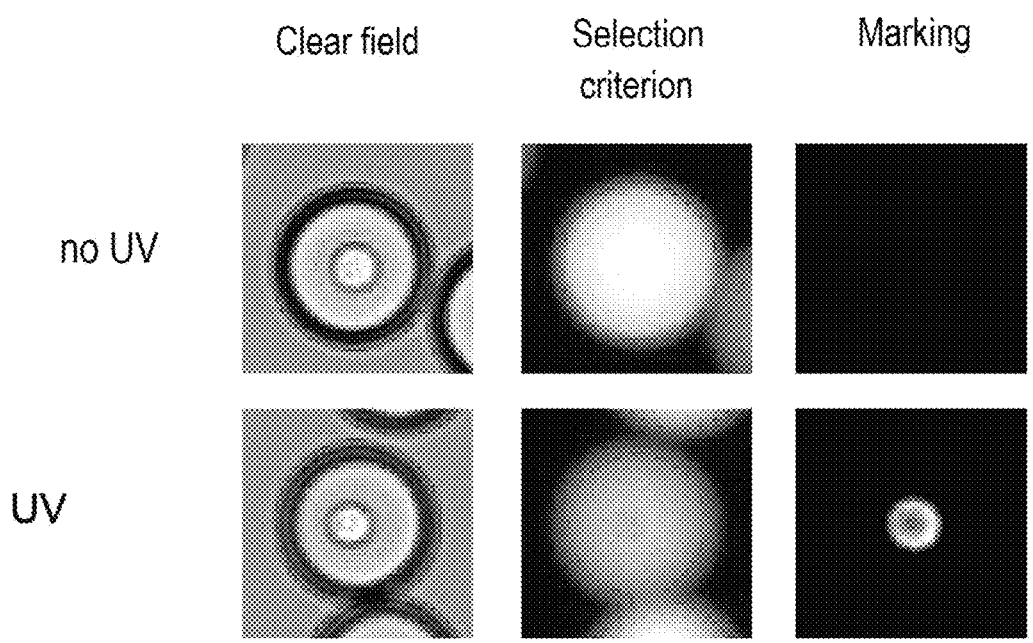
FIG. 12 illustrates a seventh example application of the system for selecting and recovering products.

A seventh nose will now be described, in reference to FIG. 12. FIG. 12 illustrates cells that have been marked using caged carboxy fluorescein-NHS. In this experiment, the selection criterion is a low concentration level of sulforhodamine. Only the drops comprising a concentration of sulforhodamine of 200 nM are tagged. The selected drops are tagged by exposing the cell to UV rays.

An eighth example will now be described. This example illustrates the tagging of cells with biotin.

In this eighth example, a solution of 10 MIO cells per milliliter is incubated with 50 micro-M of sulfo-SBED for 15 minutes on ice. The cells are recovered by centrifugation, rinsed and resuspended in a buffer solution.

The cells are separated into two batches. The first batch is exposed to ultraviolet rays for 10 seconds. The second batch is not exposed to ultraviolet rays.

Next, 5 mM of DTT, a reducing agent, is added to each batch, and the solutions are left to incubate for 30 minutes at 4 degrees Celsius.

For the second batch, for which the cells are not exposed to UV rays, the signal reagent is cleaved.

On the contrary, in the first batch, which received the UV light, the signal reagent bonds to the cell by a functional group.

Next, the cells are rinsed twice and 300 mM of streptavidin-alexa 555 is added to the cells.

It is observed that the streptavidin-alexa 555 bonds to and marks only the cells having been exposed to the UV rays.

A ninth example will now be described. This example illustrates a cytometry analysis of cells marked by fluorescence. In this experiment, cells from a cell line are withdrawn at a concentration of 10 cells per milliliter. One adds 100 microliters of a solution of 200 mM of caged fluorescein-NHS. The cells are next incubated for 30 minutes on ice, and then encapsulated in drops. A percentage, 11.34% of the cells, is exposed to the UV light and the emulsion is removed from the chamber, broken, then the cells are purified. Only the cells having been exposed to the UV light are tagged.

In order to distinguish the cells from the cell debris, the cells are incubated with a cell life marker, red calcein.

With the cytometer analysis, one measures that 9.43% of the positive cells are alive and tagged.

In another example, cells secreting IgG are tagged after detecting an IgG secretion.

The invention claimed is:

1. A method for selecting and recovering products comprising:
providing an emulsion comprising a plurality of drops contained in a carrier fluid, each drop comprising an internal fluid,
measuring at least one physical parameter for several drops of the emulsion,
classifying at least some of the drops of the emulsion in a class based on measurements obtained during the measuring,
tagging at least some of the classified drops based on the class of the drop, and
selectively recovering the drop or part of the drop using the tag of the drop or part of the drop;
wherein the internal fluid of each drop comprises a signal reagent, and the tagging comprises optical activation of the signal reagent depending on the classification of the drop.

2. The method according to claim 1, wherein a plurality of drops are classified simultaneously during the classification, and the selective recovery includes sorting the drops after tagging each classified drop.

3. The method according to claim 1, wherein the measuring comprises measuring at least one parameter reiterated at different successive moments on the same drops.

4. The method according to claim 1, wherein for each drop of a plurality of drops, the measuring comprises measuring several distinct parameters on the same drop.

5. The method according to claim 1, wherein a plurality of drops are classified during the classification in a plurality of classes, the tagging comprising illuminating each drop from a class with preset illumination conditions, the signal reagent being able to emit a light signal, advantageously fluorescence, after its activation, the drops being sorted based on their light signal level emitted during the selective recovery, the level of the light signal emitted by the signal reagent depending on illumination conditions during the activation.

6. The method according to claim 1, wherein the internal fluid of each drop comprises a signal reagent, and the tagging comprises thermal activation of the signal reagent depending on the classification of the drop.

7. The method according to claim 1, wherein the emulsion is provided in a two-dimensional chamber, the emulsion being kept in the form of a single layer of drops in the two-dimensional chamber during the measuring and the tagging.

8. The method according to claim 1, wherein a classified drop includes a cell, the tagging comprises marking the cell, and the selective recovery comprises an emulsion break followed by sorting by cytometry.

9. A system for selecting and recovering products comprising:
a support able to receive an emulsion comprising a plurality of drops contained in a carrier fluid, each drop comprising an internal fluid,
a device for measuring at least one physical parameter for several drops of the emulsion received in the support,
a classifying unit able to decide the classification of at least one drop of the emulsion based on measurements obtained during measuring,
a tagging device able to tag a drop or part of the drop based on the classification decision of the drop, and
a recovery device of the drop or part of the drop based on the tagging,
wherein the internal fluid of each drop comprises a signal reagent, and the tagging device is capable of performing an optical activation of the signal reagent depending on the classification of the drop.

10. The method according to claim 1, wherein a plurality of drops in the carrier fluid is stored in a two-dimensional chamber during measuring and the tagging, and the drops are arranged in the chamber so that no drop is superimposed on another drop.

11. A method for selecting and recovering products comprising:
providing an emulsion comprising a plurality of drops contained in a carrier fluid, each drop comprising an internal fluid,
measuring at least one physical parameter for several drops of the emulsion,
classifying at least some of the drops of the emulsion in a class based on measurements obtained during the measuring,
tagging at least some of the classified drops based on the class of the drop, and
selectively recovering the drop or part of the drop using the tag of the drop or part of the drop,
wherein the emulsion is provided in a two-dimensional chamber, the emulsion being kept in the form of a single layer of drops in the two-dimensional chamber during the measuring and the tagging.

12. A system for selecting and recovering products comprising:
a support able to receive an emulsion comprising a plurality of drops contained in a carrier fluid, each drop comprising an internal fluid,
a device for measuring at least one physical parameter for several drops of the emulsion received in the support,
a classifying unit able to decide the classification of at least one drop of the emulsion based on measurements obtained during measuring,
a tagging device able to tag a drop or part of the drop based on the classification decision of the drop, and
a recovery device of the drop or part of the drop based on the tagging,
wherein the emulsion is provided in a two-dimensional chamber, the emulsion being kept in the form of a single layer of drops in the two-dimensional chamber during the measuring and the tagging.

13. The method according to claim 3, further comprising kinetic reaction monitoring within each drop.

* * * * *